US007193096B2

(12) United States Patent
Yan et al.

(10) Patent No.: US 7,193,096 B2
(45) Date of Patent: Mar. 20, 2007

(54) PROCESS FOR PRODUCING A CONJUGATED DI- OR POLY-UNSATURATED FATTY ACID OF 12 TO 24 CARBON ATOMS OR SALT OR ESTER THEREOF

(75) Inventors: Youchun Yan, Wormerveer (NL); Krishnadath Bhaggan, Wormerveer (NL); Ulrike Schmid, Wormerveer (NL); Victoria Taran, Wormerveer (NL)

(73) Assignee: Loders Croklaan USA LLC, Channahon, IL (US)

( * ) Notice: Subject to any disclaimer, the term of this patent is extended or adjusted under 35 U.S.C. 154(b) by 116 days.

(21) Appl. No.: 10/880,080

(22) Filed: Jun. 30, 2004

(65) Prior Publication Data

US 2005/0124818 A1 Jun. 9, 2005

(30) Foreign Application Priority Data

Jul. 1, 2003 (EP) ................................ 03254185

(51) Int. Cl.
*C07C 51/347* (2006.01)

(52) U.S. Cl. .................................... 554/126; 424/78.03

(58) Field of Classification Search ................ 554/126; 424/78.03

See application file for complete search history.

(56) References Cited

U.S. PATENT DOCUMENTS 2,242,230 A 5/1941 Burr ........................... 260/398
6,160,140 A 12/2000 Bhaggan et al. ............ 554/126
6,271,404 B1 8/2001 Bhaggan et al. ............ 554/126
6,287,553 B1 * 9/2001 Alaluf et al. ............ 424/78.03
6,479,683 B1 11/2002 Abney et al. ............... 554/126
2004/0058998 A1 3/2004 Saebo et al. ................ 514/560

FOREIGN PATENT DOCUMENTS

| | | |
|---|---|---|
| EP | 0799033 | 10/1997 |
| EP | 0 839 897 B1 | 1/2001 |
| EP | 0 902 082 B1 | 7/2003 |
| WO | WO 96/18391 | 6/1996 |
| WO | WO 97/46230 | 12/1997 |
| WO | WO 00/09163 | 2/2000 |
| WO | WO 03/022964 | 3/2003 |
| WO | WO 03/080850 | 10/2003 |
| WO | WO 03/104472 | 12/2003 |

OTHER PUBLICATIONS

Sastry et al., Paint Manufacture, 40(8):32-34 (Aug. 1, 1970).
Ivanov et al., Seifen, Oele, Fette, Wachse., 99(12):328-329 (1973).
Moore, Biochemical Journal, 31:138-154 (1937).

* cited by examiner

*Primary Examiner*—Deborah D. Carr
(74) *Attorney, Agent, or Firm*—Morgan Lewis & Bockius LLP

(57) ABSTRACT

A process for producing a conjugated di- or poly- unsaturated fatty acid having from 12 to 24 carbon atoms, or a salt or ester thereof, comprises reacting a non-conjugated free fatty acid, or a salt or ester thereof, with a base in the presence of a solvent comprising a monohydric alcohol having from 1 to 6 carbon atoms, wherein the reaction is carried out at a temperature of from 120° C. to 200° C. in the presence of water in an amount of at least 4% by weight based on alcohol.

19 Claims, 1 Drawing Sheet

PROCESS FOR PRODUCING A CONJUGATED DI- OR POLY-UNSATURATED FATTY ACID OF 12 TO 24 CARBON ATOMS OR SALT OR ESTER THEREOF

BACKGROUND OF THE INVENTION

1. Field of the Invention

This invention relates to a process for producing a conjugated di- or poly-unsaturated fatty acid having from 12 to 24 carbon atoms, or a salt or ester thereof, and to the product of the process.

2. Description of Related Art

Conjugated isomers of long chain polyunsaturated fatty acids are known to have potential benefits, for example when used in food products. Examples of such acids include the linoleic acid isomers; typically, the cis 9, trans 11 and trans 10, cis 12 isomers are the most abundantly present in these materials, in general in a 1:1 weight ratio. The conjugated isomers can be produced from the corresponding non-conjugated fatty acids.

EP-A-0799033 discloses a process for producing conjugated isomers in which ethylene glycol is used. Ethylene glycol however has the disadvantage that it is very difficult to remove completely from the reaction product of the isomerisation process. Moreover, the yields of desired conjugated polyunsaturated isomers in the reaction product of the conversion in the presence of base are relatively low.

According to WO 97/46230, conjugated linoleic acids can be obtained by isomerisation of linoleic acid or safflower oil by subjecting the starting material to base (KOH) in propylene glycol at 180° C. The reaction product contains relatively large amounts of isomers other than the desired conjugated linoleic isomers. This may be due to the severe reaction conditions. EP-A-0839897 also describes a process for producing conjugated linoleic acids by subjecting fats containing linoleic acid to base in propylene glycol.

EP-A-0902082 discloses a process for the preparation of materials comprising mainly conjugated isomers of long chain polyunsaturated fatty acids wherein an oil or a free fatty acid composition or an alkyl ester composition thereof, containing at least 25 wt % of at least one isomer other than the conjugated isomers of long chain polyunsaturated fatty acids, is subjected to a treatment with a base in a solvent and wherein the solvent is an alcohol with at least 3 C-atoms and at least two hydroxy groups having: a ratio of number of C-atoms: number of OH groups of at least 1.25 but less than 3.5, preferably from 1.5 to 2.75, while the reaction is carried out between 100 and 180° C., more preferably between 120 and 180° C.

It would be desirable that the process for producing conjugated fatty acids uses a solvent system that is less costly and easier to handle than the solvents used in the prior art.

U.S. Pat. No. 2,242,230 discloses a process for producing conjugation in unconjugated polyenes. The process is carried out under non-aqueous conditions and any water that is formed in the process is removed from the reaction. The process is carried out in the presence of a base which is an alcoholic solution of dry KOH in dry alcohol or a solution of an alkali metal alkoxide in alcohol formed by reaction of the alkali metal with the alcohol. The presence of water is avoided since the document teaches that water inhibits the reaction and reduces the yield.

Sastry et al, "Isomerised Safflower Oil", Paint Manufacture, vol 40, no 8, 1 Aug. 1970, pages 32 to 34 describes the isomerisation of safflower oil followed by elaidinisation to obtain tram, trans isomers. The reaction is carried out at 210–215° C. and substantial amounts of trans, trans isomers are obtained during the first isomerisation step.

Moore, "Specroscopic changes in fatty acids", Biochemical Journal, vol 31, 1937, pages 138–154 relates to the changes in UV absorption spectra of fats treated with sodium hydroxide. Following saponification, the fats are refluxed for 24 hours.

U.S. Pat. No. 6,479,683 discloses a process for producing conjugated fatty acid esters by the reaction of an ester with an alkali metal alkoxide catalyst in a monohydric alcohol. It is evident from the materials used that the process is carried out in the absence of water.

SUMMARY OF THE INVENTION

We have discovered that when the process is carried out under anhydrous conditions, the anhydrous reaction can give rise to undesirable by-products, including dialkyl ketones (DAKs). Moreover, the reaction mixture becomes very viscous and is difficult to stir on a larger scale.

DETAILED DESCRIPTION OF THE INVENTION

Figure 1:
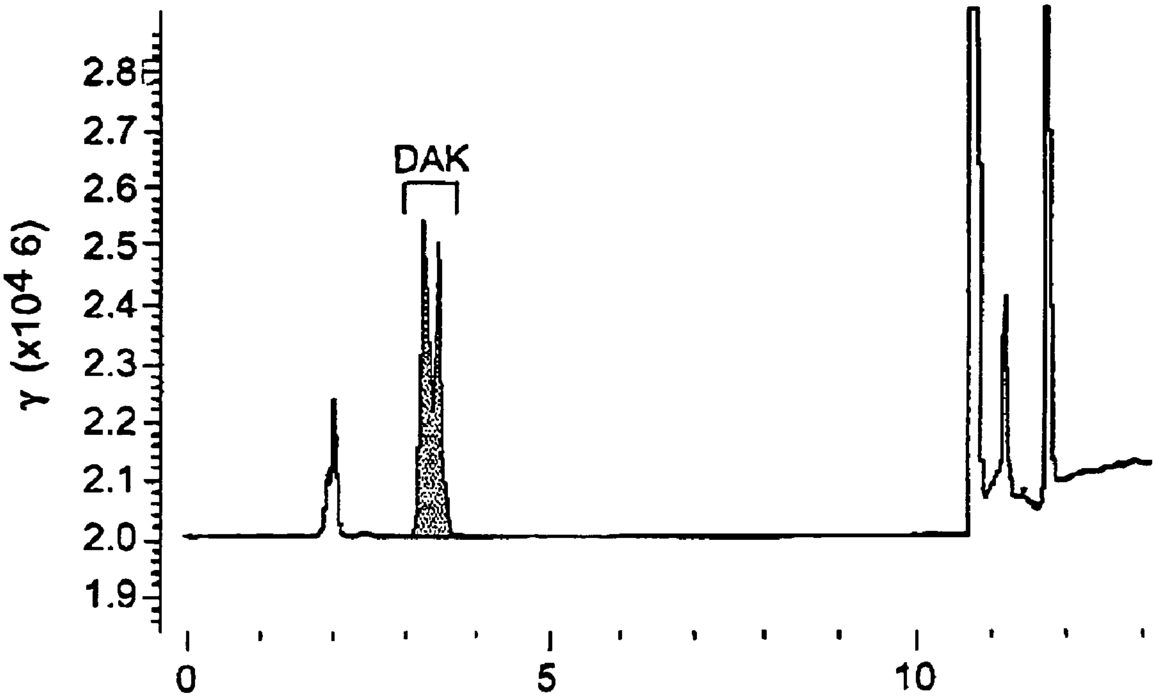
FIG. 1 which shows the HPLC separation of DAKs using Econosphere Silica column (150×4.6 mm; 3 μm) and Evaporative Light Scattering Detection.

We have now found a process for producing conjugated di- or poly-unsaturated fatty acids having from 12 to 24 carbon atoms, or salts or esters thereof, which employs ethanol as solvent but which avoids the disadvantages of the prior art process described above. Contrary to the teaching of U.S. Pat. No. 2,242,230, we have found that the disadvantages are ameliorated by including water in the reaction system and, surprisingly, that the presence of water at certain levels has little or no inhibitory effect on the formation of the conjugated fatty acids. Unexpectedly, the reaction in ethanol also proceeds faster than the reaction in the other solvent systems of the prior art. The process has advantages if carried out at a temperature in the range of from 120° C. to 200° C. This combination of process conditions allows increased yield and/or a reduction in the amount of undesirable geometric isomers (such as trans, trans isomers) and/or a reduction in the amount of undesirable side products (such as dialkyl ketones (DAKs)).

According to the present invention, there is provided a process for producing a conjugated di- or poly-unsaturated fatty acid having from 12 to 24 carbon atoms, or a salt or ester thereof, which comprises reacting a non-conjugated free fatty acid, or a salt or ester thereof, with a base in the presence of a solvent comprising a monohydric alcohol having from 1 to 6 carbon atoms, wherein the reaction is carried out at a temperature of from 120° C. to 200° C. in the presence of water in an amount of at least 4% by weight based on alcohol.

In another embodiment, the invention provides the product of the process of the invention.

In another aspect, the invention provides a product comprising a conjugated di- or poly-unsaturated fatty acid having from 12 to 24 carbon atoms, or a salt or ester thereof, and containing dialkyl ketones in an amount of less than 100 ppm, preferably less than 50 ppm, and esters of the conjugated fatty acid with the monohydric alcohol. Preferably, the esters are present in an amount of from 0.01% to 2% by weight.

Also contemplated by the invention is the use of water in an amount of at least 4% by weight based on alcohol as a co-solvent with a solvent comprising a monohydric alcohol having from 1 to 6 carbon atoms, in a process for producing a conjugated di- or poly-unsaturated fatty acid having from 12 to 24 carbon atoms, or a salt or ester thereof, which comprises reacting a non-conjugated free fatty acid, or a salt or ester thereof, with a base, for reducing the formation of by-products which are unacceptable in food products, such as dialkyl ketones (DAKs).

Fatty acids produced in the process of Be present invention are di- or poly-unsaturated i.e., they contain at least two carbon-carbon double bonds.

Typically, the fatty acids contain 2, 3, 4 or 5 carbon-carbon double bonds, preferably two carbon-carbon double bonds. In the products of the invention, the carbon-carbon double bonds are conjugated with each other (i.e., they are spaced from each other in the molecule by one carbon-carbon single bond). The starting materials that are used in the process comprise the corresponding non-conjugated fatty acids i.e., the carbon-carbon double bonds are separated from each other in the molecule by more than a single carbon-carbon bond and they are preferably separated from each other by one methylene group.

The term fatty acids and related terms used herein refers to carboxylic acids comprising an alkyl or alkenyl group (comprising two or more carbon-carbon double bonds) which may be branched or straight chain, but is preferably straight chain. The carboxylic acid contains from 12 to 24 carbon atoms, preferably from 14 to 22 carbon atoms, more preferably from 16 to 20 carbon atoms and most preferably 18 carbon atoms, including the carbon atom of the carboxylic acid group. The non-conjugated fatty acid and the conjugated fatty acid are preferably C18:2 fatty acids, more preferably they are linoleic acid and conjugated linoleic acid (CLA). The fatty acids can be mixtures of two or more fatty acids or isomers thereof.

The fatty acid that is produced in the process of the invention may be a free fatty acid, or a salt or ester thereof, or a mixture of two or more of these materials. Salts include salts with alkali metals and alkaline earth metals such as sodium potassium, calcium and magnesium preferably sodium or potassium. Esters include mono-, di- and triglycerides and mixtures thereof, and $C_1$ to $C_6$ alkyl esters (where the all group can be straight chain or branched). Typically, salts and free acids are produced in the process. Salts can be converted to free acids by raising the pH of the reaction mixture at the end of the process. Free acids can be converted to esters by esterification reactions that are well-known in the art.

The non-conjugated free fatty acid, or salt or ester thereof, that is used as the starting material for the process, is selected from the group consisting of vegetable oils, free acids derived from these oils and $C_1$ to $C_6$ alkyl esters of these free acids (where the alkyl group can be straight chain or branched). The non-conjugated fatty acid, or salt or ester thereof, may be present in the starting material in an amount of from 10 to 100% by weight, more preferably from 25% to 100% by weight, such as from 25% to 90% by weight. Preferred starting materials are vegetable oils, and it is more preferred that the vegetable oil is selected from sunflower oil, rape seed oil, soy bean oil, safflower oil, linseed oil and mixtures thereof. Safflower oil is a particularly preferred vegetable oil.

The process of the present invention is carried out in the presence of a solvent comprising a monohydric alcohol having from 1 to 6 carbon atoms. Preferably, the alcohol is selected from ethanol, methanol and mixtures thereof, most preferred is ethanol. The solvent further comprises water in an amount of at least 4% by weight based on alcohol. Other co-solvents may be present in amounts up to 50% by weight based on alcohol, preferably up to 40%, more preferably up to 30%, such as up to 20% or up to 10% by weight based on alcohol. However, preferably the solvent comprises substantially no co-solvents other than alcohol and water or comprises said other co-solvents in an amount of less than 5%, more preferably less than 2%, even more preferably less than 1% such as less than 0.1% by weight based on alcohol. Preferably, the amount of water is from 5% to 35% by weight based on alcohol, more preferably from 10% to 30% by weight based on alcohol, such as 15% to 25% by weight based on alcohol. The content of water refers to the total water content and includes water present in the starting materials as well as any added water. Water may be derived from water added to the system and/or may be already present in the alcohol solvent or the other starting materials in the process, including the base and the fatty acid. Therefore, depending on the water content of the starting materials, it may or may not be necessary to add water to the system. The amount of water in the process of the invention can be determined by methods well-known in the art, by analysis of the starting materials and/or the reaction mixture. A suitable example of a method for determining water content is the Karl Fischer method.

The process of the invention is carried out in the presence of a base. The base raises the pH of the reaction mixture. The base is suitably, for example, an alkali metal hydroxide selected from potassium hydroxide, sodium hydroxide and mixtures thereof. The molar ratio of base to non-conjugated free fatty acid, or salt or ester thereof, that is employed in the process is preferably from 1.07 to 3.5, more preferably from 1.2 to 2.5 even more preferably from 1.3 to 1.6.

The process conditions for carrying out the reaction can be varied depending on the desired rate and yield of the product. The reaction is typically carried out at a temperature above the normal boiling point of the alcohol (i.e., the boiling point at atmospheric pressure), although lower temperatures can be employed. Generally, the higher the temperature of the reaction, the faster is the rate at which the reaction proceeds. The reaction is carried out at a temperature of from 120° C. to 200° C., preferably from 140° C. to 180° C. When the reaction is carried out at a temperature above the boiling point of the alcohol, the reaction is carried out at a pressure above atmospheric pressure in a vessel that can withstand pressures greater than atmospheric pressure.

The process of the invention can be carried out batchwise or as a continuous process The process is suitable for use on a large scale in a suitable apparatus i.e., capable of the production of conjugated fatty acids or salts or esters thereof in an amount of over 100 kg, more preferably over 1000 kg, per day. When the process is carried out batchwise, it is preferably carried out for a time of from 1 to 10 hours, preferably 2 to 6 hours.

The process is preferably carried out for a time and at a temperature to form a product comprising more than 60% by weight, more preferably more than 70% by weight, based on total fatty acid and salt and esters thereof, of cis-9, trans-11 and trans-10, cis-12 isomers of the conjugated fatty acid.

The process can be carried out for a time and at a temperature to form a product comprising less than 3% by weight of linoleic acid and salts and esters thereof, based on total fatty acid and salts and esters thereof.

The process of the invention can result in the formation of lower amounts of trans, trans isomers of fatty acids than corresponding processes carried out using ethanol under anhydrous conditions. Preferably, the reaction produces trans, tans isomers of conjugated fatty acids in an amount of less than 5%, more preferably less than 3%, even more preferably less than 1%, said percentages being by weight based on total fatty acid and salt and esters thereof. Thus, the amount of trans, trans isomers in the conjugated fatty acid which is the product of the process is preferably less than 5%, more preferably less than 3%, even more preferably less than 1%, said percentages being by weight based on total fatty acid and salt and esters thereof.

The process of the invention is preferably carried out in the substantial absence of added microorganisms and enzymes, preferably in the absence of added microorganisms and enzymes.

The process of the invention optionally comprises one or more further steps. A suitable further step in the process includes, for example, separating conjugated fatty acid from the reaction mixture by a method comprising treatment with an acid and separation of the aqueous phase from the organic phase. Another optional her step in the process comprises purifying the conjugated fatty acid. Yet another optional banter process step comprises forming a mono-, di-, or tri-glyceride of the conjugated fatty acid.

The product of the process preferably contains relatively low amounts of dialkyl ketones (DAs). Preferably, the product contains dialkyl ketones in an amount of less than 100 ppm, more preferably less than 50 ppm, even more preferably less than 25 ppm. The dialkyl ketones are typically of the formula RR'CO, wherein R and R' are the same or different and are either saturated alkyl groups or unsaturated alkenyl groups having at least one carbon-carbon double bond (preferably one or two double bonds), the alkyl and alkenyl groups containing 12 to 24 (e.g., 12 to 20), preferably 14 to 18 carbon atoms, and being branched or straight chain, preferably straight chain. The product may also comprise esters of the conjugated fatty acid with the monohydric alcohol that is used in the process, such as, for example, ethyl esters. The plural term "esters" is used to reflect the fact that different isomers of the conjugated fatty acid will generally be present and, therefore, the product will contain different ester compounds. Typically, the product contains said esters in an amount of from 0.01% to 2% by weight, more preferably 0.1% to 1% by weight based on total fatty acid and salt and esters thereof. The determination of the level of esters in the product can be carried out by methods known to those skilled in the art.

The products of the invention are preferably suitable for use in an edible product, more preferably they are suitable for use in a food product, a food supplement or a pharmaceutical product.

The products of the invention can be used as such. Alternatively, the products of the invention can be used as the starting materials for a further modification, such as enrichment in an isomer, such as the cis 9, trams 11 or the tans 10, cis 12 isomer of conjugated linoleic acid. For example, the product may be used as the staring material for a process for enriching a mixture containing different conjugated isomers of the same long chain polyunsaturated fatty acid in one of the isomers, as described in WO 97/18320, the contents of which are incorporated herein by reference.

The products of the process may be used in a food product, food supplement or pharmaceutical product. The products of the invention are optionally used as a blend with a complementary fat. For example, the blend may comprise 0.3–95 wt %, preferably 2–80 wt %, most preferably 5–40 wt % of the product of the invention and 99.7–5 wt %, preferably 98–20 wt %, most preferably 95–60 wt % of a complementary fat selected from: cocoa butter, cocoa butter equivalents, palm oil or fractions thereof, palmkernel oil or fractions thereof, interesterified mixtures of said fats or fractions thereof, or liquid oils, selected from: sunflower oil, high oleic sunflower oil, soybean oil, rapeseed oil, cottonseed oil, fish oil, safflower oil, high oleic safflower oil, maize oil and MCT-oils. Food products (which term includes animal feed) contain a fat phase, wherein the fat phase contains the product of the invention. The food products are suitably selected from the group consisting of: spreads, margarines, creams, dressings, mayonnaises, ice-creams, bakery products, infant food, chocolate, confectionery, sauces, coatings, cheese and soups. Food supplements or pharmaceutical products may be in the form of capsules or other forms, suitable for enteral or parenteral application and comprise a product of the invention.

The process of the invention will now be described with reference to the following non-limiting examples. In the examples and throughout this specification, all percentages, parts and ratios are by weight unless indicated otherwise.

EXAMPLES

The examples include reference to FIG. 1.

FIG. 1 which shows the HLC separation of DAKs using Econosphere Silica column (150×4.6 mm; 3 μm) and Evaporative Light Scattering Detection.

General Method

A 1 liter jacketed pressure vessel was fitted with a mechanical stirrer and provided with a connector for nitrogen and a sample removing valve. The temperature of the vessel was controlled by a thermostatically-controlled oil-bath. The total heating time of the reaction mixture was about 45 minutes.

The materials that were used in the process were safflower oil, base (sodium or potassium hydroxide pellets) and as solvents: ethanol (FtOH) or propylene glycol.

The hydroxide pellets, safflower oil and the solvent were added to the reaction vessel and the obtained mixture was heated to the desired temperature while stirring at average speed under nitrogen. During the course of the reaction, samples were removed and submitted for analysis. After 6 hours, the reaction was stopped by cooling down the reaction mixture to ambient temperature. The final mixture was not worked up further in terms of splitting, drying and distillation.

The following abbreviations are used in the tables in the example:

| | Systematic name | Common name |
|---|---|---|
| C14:0 | Tetradecanoic acid | Myristic acid |
| C16:0 | Hexadecanoic acid | Palmitic acid |
| C16:1C | Cis-9 hexadecenoic acid | Palmitoleic acid |
| C18:0 | Octadecanoic acid | Stearic acid |
| CLA TT | Total trans conjugated octadecadienoic acid | |
| CL911C | Cis-9, cis-11 octadecadienoic acid | |

-continued

| | Systematic name | Common name |
|---|---|---|
| CL1012 | Cis-10, cis-12 octadecadienoic acid | |
| CL1113 | Cis-11, cis-13 octadecadienoic acid | |
| C18:1C | Cis-9 octadecenoic acid | Oleic acid |
| C18:1T | Trans-9 octadecenoic acid | |
| CLA OX | oxidised conjugated octadecadienoic acid | |
| C18:2T | trans-9, trans-12 octadecadienoic acid | |
| C18:2C | Cis-9, cis-12 octadecadienoic acid | Linoleic acid |
| C20:0 | Eicosoic acid | Arachidic acid |
| C20:1C | Cis-9 eicosenoic acid | Gadoleic acid |
| C22:0 | Docosoic acid | Behenic acid |
| SAFA | Saturated fatty acids | |
| CT.ISO CLA | Total cis-9, trans-11 and trans-10, cis-12 octadecadienoic acid | |
| 911CT CLA | Cis-9, trans-11, octadecadienoic acid | |
| 1012TC CLA | trans-10, cis-12 octadecadienoic acid | |
| TCLA | Total conjugated octadecadienoic acid | |

Example 1

A comparison was carried out between reactions carried out in 96% ethanol (according to the invention), and 99.9% ethanol (dry ethanol, comparative example). Both reactions were catalysed by sodium hydroxide, which was used in the form of dry pellets. Safflower oil was used as source for linoleic acid. The sample removed at t=0 hr is the first sample taken when the desired temperature was reached.

| Reaction conditions: | |
|---|---|
| Safflower oil | 275 ml |
| NaOH | 65.45 g |
| 96% or dry EtOH | 275 ml |
| Temperature (° C.): | 150 |
| Pressure (bar): | 10 |
| % [$H_2O$]: | 12.9* for the example using 96% EtOH<br>0 for the example using 99.9% EtOH |

*the balance of additional water was added to the dry sodium hydroxide pellets before reaction The reaction mixture was analysed by the fatty acid methyl ester (FAME) method using gas chromatography. The results for the process using 96% ethanol are set out in the following table:

| | Time [hrs] | | | | | | | |
|---|---|---|---|---|---|---|---|---|
| | | 0 | 1 | 2 | 3 | 4 | 5 | 6 |
| C14:0 | 0 | 0.1 | 0.1 | 0.1 | 0.1 | 0.1 | 0.1 | 0.1 |
| C16:0 | 0.1 | 5.3 | 5.3 | 5.2 | 5.3 | 5.3 | 5.2 | 5.3 |
| C16:1C | 5.5 | 0.1 | 0.1 | 0.1 | 0.1 | 0.1 | 0.1 | 0.1 |
| C18:0 | 2.2 | 2.2 | 2.2 | 2.2 | 2.3 | 2.2 | 2.2 | 2.2 |
| CLA TT | 0 | 0.1 | 0.2 | 0.2 | 0.3 | 0.4 | 0.5 | 0.6 |
| CL911C | 0 | 0.1 | 0.4 | 0.7 | 0.8 | 0.8 | 0.9 | 0.9 |
| CL1012 | 0 | 0.1 | 0.4 | 0.6 | 0.7 | 0.8 | 0.8 | 0.9 |
| CL1113 | 0 | 0.1. | 0.1 | 0.1 | 0.2 | 0.3 | 0.4 | 0.5 |
| C18:1C | 10.5 | 10.4 | 10.4 | 10.5 | 10.6 | 10.5 | 10.5 | 10.4 |
| CLA OX | 0 | 0.1 | 0.2 | 0.2 | 0.4 | 0.3 | 0.3 | 0.4 |
| C18:2T | 0.3 | 0.3 | 0.3 | 0.4 | 0.3 | 0.4 | 0.5 | 0.6 |
| C18:2C | 80.3 | 66.1 | 40.5 | 23.1 | 12.5 | 7.3 | 4 | 2.7 |
| C20:0 | 0.3 | 0.3 | 0.3 | 0.3 | 0.4 | 0.4 | 0.4 | 0.3 |
| C20:1C | 0.2 | 0.2 | 0.2 | | 0.2 | 0.2 | 0.2 | 0.2 |
| C22:0 | 0.3 | 0.3 | 0.3 | 0.3 | 0.3 | 0.3 | 0.3 | 0.3 |
| SAFA | | 8.2 | 8.2 | 8.2 | 8.4 | 8.3 | 8.3 | 8.3 |
| CT.ISO CLA | 0 | 13.8 | 38.8 | 55.6 | 65.5 | 70.5 | 73.5 | 74.4 |

-continued

| | Time [hrs] | | | | | | | |
|---|---|---|---|---|---|---|---|---|
| | | 0 | 1 | 2 | 3 | 4 | 5 | 6 |
| 911CT CLA | 0 | 6.9 | 19.3 | 27.7 | 32.6 | 35.1 | 36.6 | 37.1 |
| 1012TC CLA | 0 | 6.9 | 19.5 | 28 | 32.8 | 35.4 | 36.8 | 37.3 |
| TCLA | 0 | 14.2 | 39.7 | 57.5 | 67.9 | 73.1 | 76.3 | 77.6 |
| Others | | 0.3 | 0.6 | 0.1 | 0.1 | 0.1 | 0.1 | 0.1 |

The results for the process using 99.9% ethanol are set out in the following table:

| | Time [hrs] | | | | | | |
|---|---|---|---|---|---|---|---|
| | 0 | 1 | 2 | 3 | 4 | 5 | 6 |
| C14:0 | 0.1 | 0.1 | 0.1 | 0.1 | 0.1 | 0.1 | 0.1 |
| C16:0 | 5.3 | 5.3 | 5.3 | 5.3 | 5.3 | 5.3 | 5.3 |
| C16:1C | 0.1 | 0.1 | 0.1 | 0.1 | 0.1 | 0.1 | 0.1 |
| C18:0 | 2.2 | 2.2 | 2.2 | 2.2 | 2.2 | 2.2 | 2.2 |
| CLA TT | 0.2 | 0.3 | 0.4 | 0.5 | 0.7 | 0.8 | 1 |
| CL911 | 0.3 | 0.7 | 0.9 | 1 | 1 | 1 | 1.1 |
| CL1012 | | 0.6 | 0.7 | 0.8 | 0.9 | 0.9 | 0.9 |
| CL1113 | 0.1 | 0.1 | 0.2 | 0.3 | 0.3 | 0.4 | 0.6 |
| C18:1C | 10.4 | 10.5 | 10.5 | 10.4 | 10.4 | 10.5 | 10.4 |
| CLA OX | | 0.3 | 0.4 | 0.3 | 0.4 | 0.2 | 0.2 |
| C18:2T | 0.3 | 0.4 | 0.5 | 0.5 | 0.6 | 0.7 | 0.8 |
| C18:2C | 57.3 | 21.9 | 7.9 | 2.9 | 1.3 | 0.7 | 0.4 |
| C20:0 | 0.3 | 0.3 | 0.3 | 0.4 | 0.4 | 0.3 | 0.3 |
| C20:1C | 0.2 | 0.2 | 0.2 | 0.2 | 0.2 | 0.2 | 0.2 |
| C22:0 | 0.3 | 0.3 | 0.3 | 0.3 | 0.3 | 0.3 | 0.3 |
| SAFA | 8.3 | 8.3 | 8.3 | 8.3 | 8.3 | 8.3 | 8.2 |
| CT.ISO CLA | 22.2 | 56.5 | 69.9 | 74.5 | 75.7 | 76.2 | 76 |
| 911CT CLA | 11.1 | 28.3 | 35.1 | 37.4 | 38 | 38.4 | 38.2 |
| 1012TC CLA | 11.1 | 28.1 | 34.9 | 37.1 | 37.7 | 37.8 | 37.7 |
| TCLA | 22.7 | 58.5 | 72.5 | 77.4 | 78.9 | 79.4 | 79.6 |
| Others | 0.6 | 0.2 | 0.1 | 0.2 | 0.2 | 0.1 | 0.2 |

When 96% ethanol was used with addition of extra water, 96.6% of C18:2c was converted in 6 hours. Using dry ethanol gave a conversion of 99.5% in 6 hours. However, the reaction mixture with the lower water content produced higher amounts of the conjugated trans, tans isomer, was very viscous and difficult to stir and to remove samples.

Example 2

An experiment was carried out to compare processes carried out using ethanol (EtOH) (according to the invention) and propylene glycol (MPG) (comparative example). These reactions were catalysed by potassium hydroxide. Safflower oil was used as source for linoleic acid. The water in the system is from the potassium hydroxide used.

| Reaction conditions: | | |
|---|---|---|
| Safflower oil | | 275 ml |
| KOH pellets | | 108 g |
| EtOH or MPG | | 275 ml |
| Temperature ° C.: | | 150 |
| Pressure (bar): | | 10–12 |
| % [$H_2O$]: | EtOH | MPG |
| | 14.6 | 5.7 |
| mole KOH: mole oil | 1.79 | 1.89 |

The results of FAME analysis of the reaction in ethanol were as follows:

| | Time [hr] | | | | | | |
|---|---|---|---|---|---|---|---|
| | 0 | 1 | 2 | 3 | 4 | 5 | 6 |
| C14:0 | 0.1 | 0.1 | 0.1 | 0.1 | 0.1 | 0.1 | 0.1 |
| C16:0 | 5.5 | 5.3 | 5.3 | 5.3 | 5.3 | 5.4 | 5.4 |
| C16:1C | 0.1 | 0.1 | 0.1 | 0.1 | 0.1 | 0.1 | 0.1 |
| C18:0 | 2.2 | 2.3 | 2.2 | 2.2 | 2.3 | 2.3 | 2.3 |
| CLA_TT | 0 | 0.5 | 0.9 | 1.2 | 1.6 | 1.8 | 2.2 |
| CL911C | 0 | 0.9 | 0.9 | 1 | 1 | 1 | 1 |
| CL1012 | 0 | 0.8 | 0.9 | 0.9 | 0.9 | 0.9 | 0.9 |
| CL1113 | 0 | 0.2 | 0.3 | 0.3 | 0.4 | 0.4 | 0.6 |
| C18:1T | 0.1 | 0 | 0 | 0 | 0.1 | 0 | 0.1 |
| C18:1C | 10.5 | 10.5 | 10.4 | 10.5 | 10.5 | 10.5 | 10.4 |
| CLA OX | 0 | 0.3 | 0.2 | 0.2 | | 0.2 | 0.2 |
| C18:2T | 0.3 | 0.6 | 0.8 | 1 | 1.1 | 1.1 | 1.2 |
| C18:2C | 80.3 | 2.8 | 0.4 | 0.3 | 0.3 | 0.3 | 0.3 |
| C20:0 | 0.2 | 0.4 | 0.4 | 0.4 | 0.4 | 0.4 | 0.4 |
| C20:1C | 0.3 | 0.2 | 0.2 | 0 | 0.2 | 0.2 | 0.2 |
| C22:0 | | 0.3 | 0.3 | 0.3 | 0.3 | 0.3 | 0.3 |
| SAFA | 8.5 | 8.4 | 8.3 | 8.3 | 8.4 | 8.4 | 8.4 |
| CT.ISO CLA | 0 | 74.6 | 76.3 | 76 | 75.1 | 75 | 74.3 |
| 911CT CLA | 0 | 36.9 | 37.7 | 37.5 | 37.3 | 37.2 | 37 |
| 1012TC CLA | 0 | 37.6 | 38.7 | 38.4 | 37.9 | 37.8 | 37.3 |
| TCLA | 0 | 77.3 | 79.6 | 79.5 | 79 | 79.3 | 79.2 |
| Others | | 0.1 | 0.1 | 0.3 | 0.3 | 0.1 | 0.1 |

The results of FAME analysis of the reaction in propylene glycol were as follows:

| | Time [hr] | | | | | | |
|---|---|---|---|---|---|---|---|
| | 0 | 1 | 2 | 3 | 4 | 5 | 6 |
| C14:0 | 0.1 | 0.1 | 0.1 | 0.1 | 0.1 | 0.1 | 0.1 |
| C16:0 | 5.5 | 5.4 | 5.5 | 5.8 | 5.5 | 5.6 | 5.6 |
| C16:1C | 0.1 | 0.1 | 0.1 | 0.1 | 0.1 | 0.1 | 0.1 |
| C18:0 | 2.2 | 2.3 | 2.2 | 2.2 | 2.2 | 2.2 | 2.2 |
| CLA TT | 0 | 0.2 | 0.3 | 0.4 | 0.5 | 0.7 | 0.8 |
| CL911C | 0 | 0.6 | 0.8 | 0.8 | 0.8 | 0.9 | 0.9 |
| CL1012 | 0 | 0.6 | 0.8 | 0.8 | 0.9 | 0.9 | 0.9 |
| CL1113 | 0 | 0.1 | 0.2 | 0.3 | 0.4 | 0.5 | 0.6 |
| C18:1T | 0:1 | 0.1 | 0 | 0 | 0 | 0.1 | 0.1 |
| C18:1C | 10.5 | 10.4 | 10.5 | 10.6 | 10.5 | 10.5 | 10.6 |
| CLA OX | 0 | 0.2 | 0.3 | 0.3 | 0.2 | 0.3 | 0.3 |
| C18:2T | 0.3 | | 0.5 | 0.6 | 0.6 | 0.7 | 0.8 |
| C18:2C | 80.3 | 20.3 | 7.5 | 2.7 | 1.3 | 0.7 | 0.5 |
| C20:0 | 0.2 | 0.4 | 0.4 | 0.3 | 0.4 | 0.3 | 0.4 |
| C20:1C | 0.3 | 0.2 | 0 | 0 | 0 | 0 | 0 |
| C22:0 | | 0.3 | 0.3 | 0.3 | 0.3 | 0.3 | 0.3 |
| SAFA | 8.1 | 8.5 | 8.6 | 8.8 | 8.6 | 8.6 | 8.6 |
| CT.ISO CLA | 0 | 58.7 | 70.2 | 74.4 | 75.8 | 75.9 | 75.7 |
| 911CT CLA | 0 | 28.9 | 34.6 | 36.8 | 37.4 | 37.5 | 37.5 |
| 1012TC CLA | 0 | 29.8 | 35.6 | 37.6 | 38.4 | 38.3 | 38.2 |
| TCLA | 0 | 60.4 | 72.6 | 77 | 78.6 | 79 | 79.1 |

When 96% ethanol was used as solvent, 99.5% of C18:2c was converted in 2 hours. Using propylene glycol gave a conversion of 90.7% in 2 hours. 99.4% conversion was only obtained after stirring the mixture for 5 hours.

Example 3

A series of five experiments was carried out using safflower oil (300 g), potassium hydroxide pellets and 96% ethanol (250 ml) as the solvent. The amount of potassium hydroxide was varied (72.6 g, 77.5 g, 85.3 g, 103 g and 120.6 g). Since the pellets used contain about 15% water, the water content also varied as a result of varying the amount of potassium hydroxide.

The amount of water used in the examples was 10.9%, 11.3%, 11.9%, 13.3% and 14.6%. A measurement of the conversion of linoleic acid showed that the rate of reaction increased with increasing water content, at these levels of water content.

Example 4 Comparative Example

A comparative example was carried out to show the formation of trans, trans isomers at temperatures outside the claimed range.

Saffower oil (200 g), caustic soda (45 g) and 95–97% ethyl alcohol (450 ml) were heated under a pressure of 30–32 bar at 210–215° C. for 4 hours. Samples of the reaction mixture were taken at the start of the reaction and at 2 and 4 hours. The reaction mixture was analysed by the fatty acid methyl ester (FAME) method using gas chromatography. The results for the trans, trans conjugated isomer of CLA were as follows:

| | |
|---|---|
| 0 hours | 0.9% |
| 2 hours | 13.6% |
| 4 hours | 20.9% |

Example 5 (Analysis of DAKs)

A product produced according to the invention was analysed and found to contain 23 ppm DAKs.

Seven commercially available products were analysed for their DAK content. The results were as follows:

| Sample | DAKs (ppm) |
|---|---|
| Invention | 23 |
| Commercial product 1 | 411 |
| Commercial product 2 | 142 |
| Commercial product 3 | 135 |
| Commercial product 4 | 2365 |
| Commercial product 5 | 4118 |
| Commercial product 6 | 4713 |
| Commercial product 7 | 5340 |

The following is a general method for analysis of DAKs.

Analysis of Dialkyl Ketones (DAKs)

The sample is saponified with an ethanolic potassium hydroxide solution. The unsaponifiables are extracted with petroleum ether. After washing the solvent is evaporated and the residue dissolved in a mire of toluene and hexane. This solution is analysed on a Silica straight phase HPLC system with an Evaporative Light Scattering Detector.

Reagents and Materials ethanol (analytical grade)

potassium hydroxide (analytical grade)

petroleum ether (40–65)

distilled water sodium chloride (analytical grade)

hexane (analytical grade)

toluene (analytical grade)

ethyl acetate (analytical grade)

formic acid (analytical grade)

2 M ethanolic KOH: dissolve 35 gram KOH in 25 ml water under a gentle flow of nitrogen. Allow the solution to cool down to room temperature and dilute with ethanol to 250 ml.

DAK primary solution: Weigh out 25 mg DARK in a 100 ml flask. Dissolve the material in a mixture of toluene/hexane (1:1). Record the weight of the solvent.

DAK dilution 1: Pipette 2 ml of the primary solution in a 10 ml flask and record the weight of the solution. Dilute with toluene/hexane (1:1) and record the weight of the solvent.

DAK dilution 2: Pipette 2 ml of the DAK dilution 1 in a 10 ml flask and record the weight of the solution. Dilute with toluene/hexane (1:1) and record the weight of the solvent.

Apparatus and Equipment 20 ml test-tube with screw cap

1000 μl Eppendorf pipette analytical balance water bath shaker 2 and 24 ml vials heating block Pre-Treatment The sample has to be heated until fully melted. Avoid overheating of the sample. In this state tae sample should be clear. Moisture should be removed by adding $Na_2SO_4$.

Calibration Curve

Transfer some of the diluted DAK solutions 1 and 2 to HPLC auto sampler vials. Fill a vial with some of the hexane/toluene (1:1) mixture to be used as blank. Set up the auto sampler to, inject the following sequence: blank (20 μl), DAK solution 2 (20, 40, 60 and 80 μl), DAK solution 1 (20, 40, 60 and 80 μl). Set up a calibration curve by plotting the amount of DAK to the peak area (see: Quantification).

Saponification

Pipette 1000 μl of sample in a test-tube and record the weight. Add 10 ml 2 N ethanolic KOH solution and some boiling stones. Close the vial firmly and heat the solution for 20 minutes at 90° C. Cool the test-tube to room temperature, add approximately 10 ml of water and shake. If necessary, the sample can be heated to dissolve the soaps.

Add 5 ml petroleum ether and mix the solution several times with a shaker. Pipette a few ml of a saturated aqueous. NaCl solution in order to obtain clear separation. Transfer the complete petroleum ether layer to a second test-tube. Repeat the extraction two times and collect all petroleum ether in the secondary test-tube.

Add 10 ml of a water/ethanol (1:1) solution to the combined petroleum ether and mix the solution several times with the aid of a shaker. Wait until two layers are visible before adding 2×2 ml of a saturated aqueous NaCl solution. Transfer the upper layer into a third 20 ml test-tube and repeat the washing step. Finally, transfer the petroleum ether layer very carefully to a 20 ml vial. Place the vial in a heating block and evaporate the solvent under a gentle flow of nitrogen. Pipette exactly 4 ml of a toluene/hexane (1:1) mixture in the vial and dissolve the residue. Transfer some of the sample solution to a HPLC auto sampler vial.

HPLC Analysis

The samples are analyzed on a HPLC system under the following conditions:

solvents:

A: hexane

B: ethylacetate

C: toluene (2.5 ml/l formic acid)

All solvents should be HPLC grade with exception of the formic acid. Mix the formic acid thoroughly to make sure the acid is well dissolved.

TABLE

HPLC gradient for the separation of DAK in unsaponifiable using an Alltech Econosphere Silica HPLC column (150 × 4.6 mm; 3 μm)

| Time(min) | Flow(ml/min) | Solvent A | B | C | Curve |
|---|---|---|---|---|---|
| 0 | 0.9 | 50 | 0 | 50 | 6 |
| 5 | 0.9 | 50 | 0 | 50 | 6 |
| 8 | 0.9 | 0 | 25 | 75 | 6 |
| 10 | 0.9 | 0 | 25 | 75 | 6 |
| 13 | 0.9 | 50 | 0 | 50 | 6 |
| 25 | 0.9 | 50 | 0 | 50 | 6 |

flow: 0.9 ml/min
runtime: 25 min
injection volume: 20 μl
detector: ELSD (drift-tube: 75° C.; nebulizer: 1.75 SLPM nitrogen)

Quantification

Peak identification—See FIG. 1 which shows the HPLC separation of DAK in unsaponifiable using Econosphere Silica column (150×4.6 mm; 3 μm) and Evaporative Light Scattering Detection.

Calculation

Calculate the amount of DAK that has been injected expressed in ng. Set up a calibration curve by plotting the peak area (γ) again the calculated amount of DAK (x) using the following equation. The amount of DAK, present in the sample (DAK(ng)) can be found by interpolation of the peak area into the calibration curve.

$$y=a \times x^{e}$$

The amount of DAK can be calculated by:

$$DAK(mg/kg)=(DAK(ng)\times V(ml))\div(v(\mu l)\times \text{sample}(g))$$

The invention claimed is:

1. A process for producing a conjugated di- or poly-unsaturated fatty acid having from 12 to 24 carbon atoms, or a salt or ester thereof, which comprise reacting a non-conjugated free fatty acid, or a salt or ester thereof, with a base in the presence of a solvent comprising a monohydric alcohol having from 1 to 6 carbon atoms, wherein the reaction is carried out at a temperature of from 120° C. to 200° C. in the presence of water in an amount of at least 4% by weight based on alcohol.

2. Process as claimed in claim 1, wherein the alcohol is selected from the group consisting of ethanol, methanol and mixtures thereof.

3. Process as claimed in claim 1, wherein the base is an alkali metal hydroxide selected from the group consisting of potassium hydroxide, sodium hydroxide and mixtures thereof.

4. Process as claimed in claim 1, wherein the amount of water is from 5% to 35% by weight based on alcohol.

5. Process as claimed in claim 1, wherein the amount of water is from 10% to 30% by weight based on alcohol.

6. Process as claimed in claim 1, wherein the conjugated fatty acid contains less than 5% by weight of trans, trans isomers.

7. Process as claimed in claim 6, wherein the reaction is carried out at a temperature of from 140° C. to 180° C.

8. Process as claimed in claim 1, wherein the molar ratio of base to non-conjugated free fatty acid, or salt or ester thereof, is from 1.07 to 3.5.

9. Process as claimed in claim 1, wherein the non-conjugated free fatty acid, or salt or ester thereof, is selected from the group consisting of vegetable oils, free acids derived from these oils and $C_1$ to $C_6$ alkyl esters of these free acids.

10. Process as claimed in claim 9, wherein the vegetable oil is selected from the group consisting of sunflower oil, rape seed oil, soy bean oil, safflower oil, linseed oil and mixtures thereof.

11. Process as claimed in claim 1, wherein the non-conjugated fatty acid and the conjugated fatty acid are C18:2 fatty acids.

12. Process as claimed in claim 11, wherein the process is carried out for a time and at a temperature to form a product comprising more than 70% by weight based on total fatty acid and salt and ester thereof, of cis-9, trans-11 and trans-10, cis-12 isomers of the conjugated fatty acid.

13. Process as claimed in claim 11 or claim 12, wherein the process is carried out for a time and at a temperature to form a product comprising less than 3% by weight of linoleic acid and salts and esters thereof, based on total fatty acid and salt thereof.

14. Process as claimed in claim 1, which further comprises separating conjugated fatty acid from the reaction mixture by a method comprising treatment with an acid and separation of the aqueous phase from the organic phase.

15. Process as claimed in claim 1 which further comprises the step of purifying the conjugated fatty acid.

16. Process as claimed in claim 1 which further comprises the step of forming a mono-, di-, or tri-glyceride of the conjugated fatty acid.

17. Process as claimed in claim 6 wherein the conjugated fatty acid contains less than 1% by weight of trans, trans isomers.

18. Process as claimed in claim 8 wherein the molar ratio of base to non-conjugated fatty acid, or salt or ester thereof, is from 1:3 to 1:6.

19. Process as claimed in claim 12 wherein the process is carried out for a time and at a temperature to form a product comprising more than 80% by weight based on total fatty acid and salt and ester thereof, of cis-9, trans-11 and trans-10, cis-12 isomers of the conjugated fatty acid.

* * * * *